United States Patent
Villa et al.

[11] Patent Number: 5,646,022
[45] Date of Patent: Jul. 8, 1997

[54] PROCESS FOR THE PRODUCTION OF GAMMA NONALACTONES IN NATURAL FORM

[76] Inventors: Mario Villa, via dei Fiori 18, 13058 Ponderano; Claudio Fuganti, via G.B. Nazari 8, 20129 Milano; Gioia Zucchi, via Bezzecca 7, 22030 Oliveto Lario; Gianna Allegrone, via Tofane 44, 10141 Torino; Masimo Barbeni, corso Monte Cucco 130/D, 10141 Torino; Paolo Cabella, corso Sommeiller 17, 10128 Torino, all of Italy

[21] Appl. No.: 508,661

[22] Filed: Jul. 28, 1995

[30] Foreign Application Priority Data

Jul. 28, 1994 [IT] Italy ................... TO94A0628

[51] Int. Cl.$^6$ .......................... C12P 17/08
[52] U.S. Cl. ........................ 435/124; 435/938
[58] Field of Search ..................... 435/124, 938

[56] References Cited

U.S. PATENT DOCUMENTS 4,950,607 8/1990 Cardillo et al. .................. 435/121
5,168,054 12/1992 Cardillo et al. .................. 435/125

*Primary Examiner*—Herbert J. Lilling
*Attorney, Agent, or Firm*—Dechert Price & Rhoads

[57] ABSTRACT

Gamma lactones with 9 carbon atoms, saturated or unsaturated and mixtures thereof, in natural form, are obtained by:

A) culturing a microorganism selected from the group comprising *Pichia ohmeri* and *Pichia stipitis* or both of these in a substrate comprising an unsaturated $C_{18}$ hydroxy-acid with the hydroxyl in position $C_{13}$ to obtain a mixture comprising gamma nonanolide;

or, alternatively,

B) subjecting to lipoxygenation a substrate comprising an acid selected from the group comprising linoleic acid and linolenic acid or mixtures thereof and distilling the product of lipoxygenation in a current of steam to obtain a mixture comprising an unsaturated gamma lactone that is gamma-2-nonenolide, gamma-2,6-nonadienolide or mixtures thereof.

12 Claims, No Drawings

PROCESS FOR THE PRODUCTION OF GAMMA NONALACTONES IN NATURAL FORM

TECHNICAL FIELD

The present invention relates to a process for the production of saturated or unsaturated gamma lactones with nine carbon atoms.

BACKGROUND ART

The recent introduction of a statutory distinction between natural flavourings and those that have an identical chemical structure but are synthesised (U.S. Code of Federal Regulations 21: 101.22.a.3, EC Directive 88/388 and D.L. 25 Jan. 1992 No. 107) has made it worthwhile to produce substantial quantities of non-accessible flavouring agents by extracting them from natural sources by biodegrading natural products (D. W. Armstrong in Flavor Chemistry. Trends and Developments, Ed. R. Teranishi, R. G. Buttery, F. Shahidi; ACS Symposium Series 383, American Chemical Society, Washington D.C., 1989, p.105–120). These products are preferred by the consumer and add value to the foods to which they are added; it is therefore desirable for them to be produced by these methods.

Some of the most important of these flavouring products are gamma and delta lactones from $C_6$ to $C_{12}$, which can be either saturated or mono- or polyunsaturated, with the unsaturation of the ring in various positions in the chain. These are the key constituents of many fruit flavourings and milk products. They are generated in fruit in extremely small quantities, generally at the time of ripening. It is uneconomical to extract lactones for use as flavourings from natural sources because of the low concentration in which they are present and because the concentration depends on the degree of ripening and many other factors that are difficult to control.

Hence, in recent years, to meet the demand for natural lactones, many microbiological processes have been developed in which natural precursors of lactones, comprising hydroxylated derivatives of natural fatty acids, are degraded to gamma and delta lactones depending on the position of the hydroxyl in relation to the carboxyl in the precursor used.

Gamma decanolide is produced in this way from ricinoleic acid (U.S. Pat. No. 4,560,656 and European Patent EP-B-0 258 993). Other lactones with an even number of carbon atoms are obtained by the microbial biodegradation of the products of photooxidation/reduction of oleic, linoleic and linolenic acids as described in EP 90402217.5.

In all these cases, the lactones obtained contain an even number of carbon atoms. This is due to factors affecting biosynthesis. The hydroxylated natural precursors obtained from unsaturated $C_{18}$ or $C_{16}$ acids have an even number of carbon atoms and, if the degradation is effected by beta oxidation with the removal of two carbon atoms as S-acetyl CoA, lactones with an even number of carbon atoms are obtained.

The proposed degradation scheme is as follows:

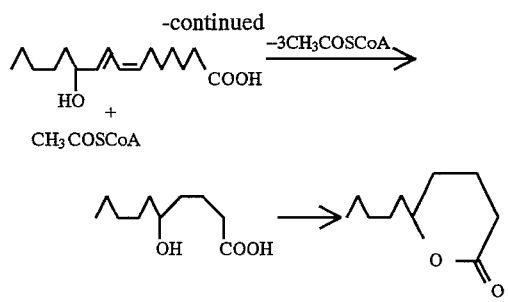

However, gamma and delta lactones with an odd number of carbon atoms exist in nature. Of these, gamma-nonanolide (1) and gamma-2-nonenolide (2) are particularly important; their structural formulae are shown below:

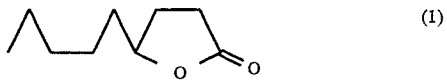 (1)

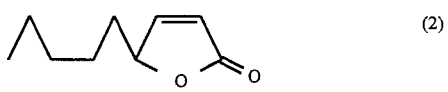 (2)

These two products are minor constituents of *Dipteryx odorata* (tonca bean) (M. Woerner et al. in Unters. Forsch. 1991, 193, 21). Gamma-nonalactone is also a known constituent of the apricot, the strawberry, the blackberry, the peach and many other fruits. In the synthetic racemic form, gamma nonanolide is widely used in the food flavouring industry, for example as a constituent of fruit flavours. However, despite the importance of these lactones with an odd number of carbon atoms, there are no natural processes capable of supplying substantial quantities of product in an optically active form.

SUMMARY OF THE INVENTION

The present invention is based on the discovery that lactones with nine saturated or unsaturated carbon atoms can be obtained from natural precursors by enzymatic processes.

Hence the object of the present invention is a process for the production of saturated or unsaturated gamma nonalactones or mixtures of these, characterized in that it involves:

A) culturing a microorganism selected from the group comprising *Pichia ohmeri* and *Pichia stipitis* or both of these in a substrate comprising an unsaturated $C_{18}$ hydroxy-acid with the hydroxyl at $C_{13}$, or a glyceride containing it, to obtain a mixture comprising gamma nonalide;

or alternatively:

B) subjecting to lipoxygenation a substrate comprising an acid selected from the group comprising linoleic acid and linolenic acid or mixtures of these and distilling the product of lipoxygenation in a current of steam to obtain an unsaturated gamma lactone that is either gamma-2-nonenolide or 2,6-nonadienolide or a mixture of these.

DETAILED DESCRIPTION OF THE INVENTION AND PREFERRED EMBODIMENTS

With reference to process variant (A) above, the use of coriolic acid (R) is particularly preferred. In particular, it has been found that the microbiological degradation of coriolic acid (3), when microorganisms such as *Pichia stipitis* and *Pichia otuneri* are used, yields a mixture of gamma nonanolide (1) and delta decanolide (4), presumably according to the reaction chain below:

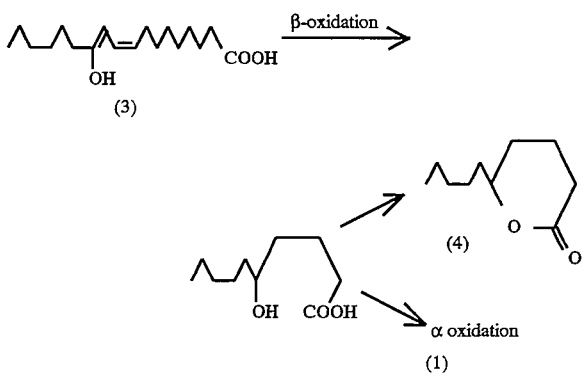

It was found completely unexpectedly that the yield of gamma nonanolide (1) in relation to that of delta decanolide (4) is much greater when the enantiomeric form (R) of coriolic acid (3) is used. Multidimensional chiral GLC analysis indicates that the gamma nonanolide (1) produced in this way comprises mainly the enantiomer (R), as does the delta decanolide (4) that accompanies it. Coriolic acid (R) for use as the substrate is easily obtainable from the oleaginous seeds of plants such as those of the genus Coriaria.

When coriolic acid (S) is used as the substrate, the yield of gamma nonanolide (1) in the (S) form is much lower.

Other substrates that are suitable for the preparation of gamma nonanolide are mixtures of hydroxy-acids containing coriolic acid obtained by photooxidation/reduction or lipoxygenation/reduction of linoleic acid alone or mixed with other unsaturated fatty acids such as oleic acid. However, the ratio of gamma nonanolide to other lactones produced when the above microorganisms are cultured in these substrates, the most abundant of which is delta decanolide, is relatively small. This renders the process less favourable since it is necessary to separate the product required from the other lactones.

The photooxygenation process is known per se and is generally carried out in a solvent in the presence of a natural photoactivator, as described in detail in the method, for example in "The Lipid Handbook", Chapman & Holl, London, 1986, p.453.

The lipoxygenation process, which is known per se, is carried out with natural lipoxygenase, preferably with the enzyme system present in linseed meal.

The reduction of the product of photooxidation or lipoxygenation to produce the hydroxy-acids is preferably effected by treating it with a natural reducing agent, such as ferrous sulphate or cysteine or its salts, in an appropriate solvent, by the method described by H. D. Belitz and W. Grosch in Food Chemistry, Springer Verlag, Berlin, 1987, p.172 or H. W. Gardner, J. Agr. Food Chem. 1975, 23, 129.

The hydroxy-acids can be present in the above mixtures in the form of free acids, esters or glycerides.

Apart being of specific value for the production of substantial quantities of gamma nonanolide, the processes described above also yield mixtures of natural lactones, which can be used as flavouring constituents. The composition of these mixtures depends on the microorganism, the substrate and the incubation time. These mixtures can then be used as flavourings or can be further processed by conventional methods to separate out the desired compounds.

The process (B) described above yields mixtures of lactones with nine unsaturated carbon atoms, of which gamma-2-nonenolide (2) is of particular interest. This product is thought to be responsible for the pleasant characteristic "deep fried" taste acquired by food fried in oil (cf. H. D. Belitz and W. Grosch, Food Chemistry, Springer Verlag, 1987, p.180) and has been found in vegetable sources such as the tonca bean.

However, this is not the only use for this product. It is known that gamma-2-nonenolide is easily reduced by yeast to gamma nonanolide (G. Fronza et al., Tetrahedon Letters, 1993, 34, 6467). Hence, access to gamma-2-nonenolide provides another access route to natural gamma nonanolide, as illustrated in the reaction chain below, in which linoleic acid is used as the lipoxygenation substrate.

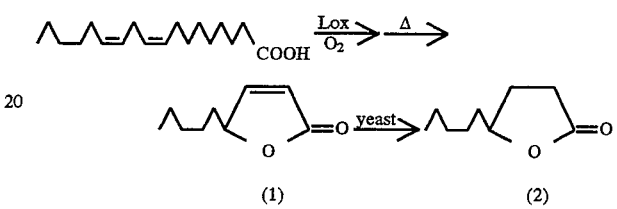

The latter conversion is also of value because the gamma-2-nonenolide (2) generated by this process contains an excess of enantiomer (S). The enantiomeric ratio remains unchanged even when the double bond is biologically saturated. This therefore provides access to gamma nonanolide with an excess of enantiomer (S) while enantiomer (R) can be obtained from coriolic acid (R).

The above conversion involving the degradation of polyunsaturated C-18 acid to unsaturated C-9 gamma lactone by the action of lipoxygenase and ambient oxygen is not limited to linoleic acid, but also takes place with linolenic acid. It has been found that when a mixture of linoleic acid and linolenic acid is subjected to the action of the above agents, the resulting product of distillation contains a mixture of $C_9$ gamma lactones of which one is the product (2) and the other is the corresponding product which has a further unsaturation in position 6 of structure (5) below.

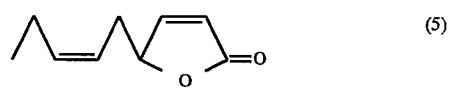

This discovery is of value not only because it enables the unsaturated lactone (5) to be obtained but also because, if the mixture obtained is fermented with yeast, a mixture of gamma nonanolide and gamma non-6-enolide (6) is obtained.

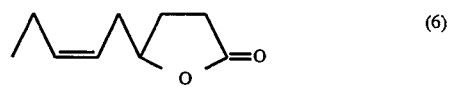

This lactone is a constituent of jasmine essence, which can therefore be derived by a biotechnological method from linolenic acid.

EXAMPLES I–IV

General Procedure for Biotransformation in *Pichia ohmeri* and *stipitis*

A sample of *P. ohmeri* (CBS 5367) and/or *P. stipitis* (CBS 5773) grown on MPGA (20 g/l malt extract, 5 g/l peptone, 20 g/l glucose, 15 g/l agar, pH 6.5–7) for three days at 28°–30° C. is used.

This is seeded in a 300 ml flat-bottomed conical flask containing 50 ml MPGB (20 g/l malt extract, 5 g/l peptone, 20 g/l glucose). The flask is placed on a stirring device (120 rpm) at 28°–30° C. for 24 hours. The resulting pre-inoculumis seeded in a ratio of 10% in 300 ml flasks containing 50 ml MPGB and left to grow under the same conditions for 24 hours. At this point the hydroxy-acid substrates are added in a concentration of 2.5 g/l. The biotransformation is left to take place under the temperature and stirring conditions described above for 24 hours and 48 hours respectively. At the end of these periods, the mycelium is filtered, being eluted several times on the filter with methylene chloride. This is then used to extract the liquid, of which the pH is increased to 4 by the addition of citric acid solution.

The substrates used were:

a) coriolic acid (R) obtained by hydrolysis with lipase from the glycerides obtained from the seeds of Coriaria.

The results obtained with this substrate and with *Pichia ohmeri* and *Pichia stipitis* respectively are shown in Table I.

TABLE I

| Incorporation of coriolic acid (R) Weight ratio of gamma nonanolide:delta decanolide | | |
|---|---|---|
| | 24 h | 48 h |
| P. ohmeri | 0.18 | 0.36 |
| P. stipitis | 2.89 | 2.63 |

(b) coriolic acid (S) obtained by lipoxygenation of linoleic acid (90% Fluka) with soya lipoxygenase (Fluka) at pH 9, using air or oxygen. On completion of the reaction a solution of sodium cysteinate is added. The reaction mixture is left to react at ambient temperature until the peroxide test is negative. The pH is adjusted to 4.5 with citric acid and the coriolic acid (S) thus obtained extracted with solvents.

The results obtained are shown in Table II.

TABLE II

| Incorporation of coriolic acid (S) Weight ratio of gamma nonanolide:delta decanolide | | |
|---|---|---|
| | 24 h | 48 h |
| P. ohmeri | 0.15 | 0.13 |
| P. stipitis | 0.19 | 0.53 |

(c) mixture of hydroxy-acids obtained as follows: 50 g linseeds are crushed to a fine meal, taking care to ensure that the mass does not undergo excessive heating during the operation. The resulting meal is suspended in a liter of pH 9 borate buffer and stirred for one hour. 3 ml/l linoleic acid are added and air or oxygen passed through for 6 hours at a temperature of 10°–15° C. Sodium cysteinate is added and the hydroxy-acids extracted as described above.

The results obtained, expressed as a weight ratio of gamma nonanolide to total lactones, are shown in Table III.

TABLE III

| Incorporation of linseed meal lipoxygenates Ratio of gamma nonanolide:total lactones | | |
|---|---|---|
| | 24 h | 48 h |
| P. ohmeri | 0.06 | 0.18 |
| P. stipitis | 0.05 | 0.36 |

(d) Mixture of hydroxy-acids obtained as follows: 10 ml linoleic acid in 100 ml methylene chloride in the presence of 1 g chlorophyll are subjected to oxidation with air while exposed to solar radiation. On completion of the reaction, the organic phase is extracted with pH 9 borate buffer. The aqueous phase containing the hydroperoxides is then treated with sodium cysteinate and the hydroxy-acids are recovered by extraction with solvent from the solution acidified with citric acid.

The results obtained, expressed as weight ratios of gamma nonanolide to total lactones are shown in Table IV.

TABLE IV

| Incorporation of photooxidation products Ratio of gamma nonanolide:total lactones | | |
|---|---|---|
| | 24 h | 48 h |
| P. ohmeri | 0.17 | 0.14 |
| P. stipitis | 0.66 | 0.16 |

EXAMPLES V AND VII

General procedures for the production of 2-nonenolide (2) and 2,6-nonadienolide (5) from linoleic and linolenic acid by the action of lipoxygenase Linoleic acid and a mixture of linoleic and linolenic acid respectively are subjected to lipoxygenation at ambient temperature at pH 9 with soya lipoxygenates (Fluka) at the rate of 2 ml/l and 100 mg lipoxygenase for 24 hours, using air or oxygen. At the end of the incubation period, the products are extracted by steam distillation, the yield being approximately 500 ml. The aqueous phase thus obtained is extracted with solvent. This is evaporated off to give 0.3–1.1 g of a mixture of products with the composition shown in Table V for the initial substrate comprising linoleic acid and in Table VII for the mixture of linoleic and linolenic acids. Table V shows the results of 5 significant tests performed by the procedure described above.

TABLE V

| Test no | Gas chromatographic percentages in the distilled oil | | | | |
|---|---|---|---|---|---|
| | V.1 | V.2 | V.3 | V.4 | V.5 |
| non-2-enolide | 27.4(R/S = 29/71) | 16.5 R/S = 26/74) | 24.1 (R/S = 19/81) | 5.9 (R/S = 31/69) | 6.6 (R/S = 23/77) |
| nonanolide | 0.45 | 1.30 | 0.43 | 0.19 | 0.82 |

TABLE VII

| | % | R | S |
|---|---|---|---|
| gamma-2-nonenolide | 2.58 | — | — |
| gamma-2,6-nonadienolide | 3.19 | 54 | 46 |

EXAMPLE VI

Procedure for the reduction of unsaturated gamma lactones with yeast 20 g baker's yeast (Distillerie Italiane) in 200 ml water and 5 g glucose are stirred for 10 minutes at ambient temperature. The mixtures of lactones with the compositions shown in Tables V and VII are added and stirring continued for 24 hours. The products are recovered by steam distillation, which yields approximately 150 ml distillate. This is extracted to give the mixture with the composition shown in Table VI a) for the initial substrates V.3 and V.4 in Table V and Table VI b) for the initial mixture in Table VII.

TABLE VI

| Substrate | gamma-nonanolide | | |
|---|---|---|---|
| | % | R | S |
| V.3 | 24.13 | 19 | 81 |
| V.4 | 5.83 | 31 | 69 |
| VI | 38.17 | 35 | 65 |

We claim:

1. Process for the production of gamma lactones with 9 carbon atoms, saturated or unsaturated or a combination thereof, characterized in that it involves culturing a microorganism selected from the group comprising *Pichia ohmeri* and *Pichia stipitis*, or both of these, in a substrate comprising an unsaturated $C_{18}$ hydroxy-acid, wherein the hydroxyl is at $C_{13}$, or a glyceride containing such an hydroxy-acid to yield a mixture comprising gamma lactones with 9 carbon atoms, saturated or unsaturated or a combination thereof, and recovering said mixture comprising said gamma lactones from the culture.

2. Process according to claim 1, in which said substrate contains R-coriolic acid.

3. Process according to claim 1, in which said substrate is a product obtained by photo-oxidation/reduction of linoleic acid or a mixture of saturated $C_{18}$ fatty acids comprising linoleic acid.

4. Process according to claim 1, in which said substrate is a product obtained by lipoxygenation and reduction of linoleic acid or a mixture of unsaturated $C_{18}$ fatty acids comprising linoleic acid.

5. Process according to claim 4, in which the lipoxygenation is effected with an enzyme system present in linseed meal.

6. Process according to claim 3, in which the reduction of the product of photo-oxidation or lipoxygenation is effected with ferrous sulphate or cysteine or a salt thereof.

7. Process according to claim 4, in which the reduction of the product of photo-oxidation or lipoxygenation is effected with ferrous sulphate or cysteine or a salt thereof.

8. Process according to claim 1, in which the microorganisms is *Pichia stipitis*.

9. Process according to claim 1, in which a selected gamma lactone with 9 carbon atoms is extracted from said mixture comprising gamma lactones.

10. Process according to claim 1, in which said gamma lactones comprise gamma nonanolide.

11. Process according to claim 10, in which said gamma lactones comprise gamma nonanolide and gamma non-6-enolide.

12. Process according to claim 2, in which said gamma lactones comprise R-gamma nonanolide.

* * * * *